United States Patent
Hirt et al.

(10) Patent No.: US 8,529,577 B2
(45) Date of Patent: Sep. 10, 2013

(54) INSTRUMENT SET FOR FIXING AN IMPLANT IN A BONE

(75) Inventors: Hubert Hirt, Freiburg (DE); Sascha Berberich, Tuttlingen (DE)

(73) Assignee: Karl Storz GmbH & Co. KG (DE)

(*) Notice: Subject to any disclaimer, the term of this patent is extended or adjusted under 35 U.S.C. 154(b) by 1279 days.

(21) Appl. No.: 11/538,931

(22) Filed: Oct. 5, 2006

(65) Prior Publication Data
US 2007/0123887 A1    May 31, 2007

Related U.S. Application Data

(63) Continuation of application No. PCT/EP2005/003431, filed on Apr. 1, 2005.

(30) Foreign Application Priority Data

Apr. 7, 2004  (DE) .................... 10 2004 018 426

(51) Int. Cl.
*A61B 17/56* (2006.01)
*A61F 2/08* (2006.01)

(52) U.S. Cl.
USPC ............ 606/98; 606/80; 606/86 R; 623/13.14

(58) Field of Classification Search
USPC .............. 606/86 R, 87–88, 98, 263, 80, 96, 606/97, 104; 623/13.11, 13.12, 13.18, 13.13, 623/13.14
See application file for complete search history.

(56) References Cited

U.S. PATENT DOCUMENTS

| 3,973,277 | A | | 8/1976 | Semple et al. ............. 623/13.14 |
|---|---|---|---|---|
| 5,151,104 | A | * | 9/1992 | Kenna ........................... 606/328 |
| 5,354,300 | A | * | 10/1994 | Goble et al. ..................... 606/80 |
| 5,437,675 | A | * | 8/1995 | Wilson ............................. 606/80 |
| 5,704,936 | A | * | 1/1998 | Mazel ........................... 606/254 |
| 6,540,783 | B1 | | 4/2003 | Whittaker et al. ......... 623/13.14 |
| 6,712,849 | B2 | * | 3/2004 | Re et al. ..................... 623/13.14 |
| 2003/0023268 | A1 | * | 1/2003 | Lizardi ........................ 606/232 |
| 2003/0065391 | A1 | | 4/2003 | Re et al. ..................... 623/13.14 |
| 2003/0216780 | A1 | * | 11/2003 | Fitts et al. ..................... 606/232 |
| 2004/0243135 | A1 | * | 12/2004 | Koseki ........................... 606/80 |

FOREIGN PATENT DOCUMENTS

| DE | 38 03 208 | 10/1989 |
|---|---|---|
| DE | 42 06 640 | 11/1993 |
| DE | 299 22 088 | 4/2000 |
| EP | 0 279 129 | 8/1988 |
| EP | 0 425 140 | 5/1991 |
| WO | WO 94/15556 | 7/1994 |

OTHER PUBLICATIONS

English Translation of the International Preliminary Report on Patentability, Nov. 14, 2006, 7 pages.
International Search Report; Sep. 14, 2005; 3 Pages.

* cited by examiner

*Primary Examiner* — Michael T Schaper
(74) *Attorney, Agent, or Firm* — St. Onge Steward Johnston & Reens LLC

(57) ABSTRACT

An instrument set for fixing a cord-like implant in a bone comprises a retaining element which can be inserted into the bone. The retaining element comprises a recess for receiving a transverse pin and is also used to fix the implant. In addition, the retaining element comprises a guide for receiving the implant, the guide being configured in such a way that the implant can be guided in a loop formation around the transverse pin distally from the retaining element.

28 Claims, 10 Drawing Sheets

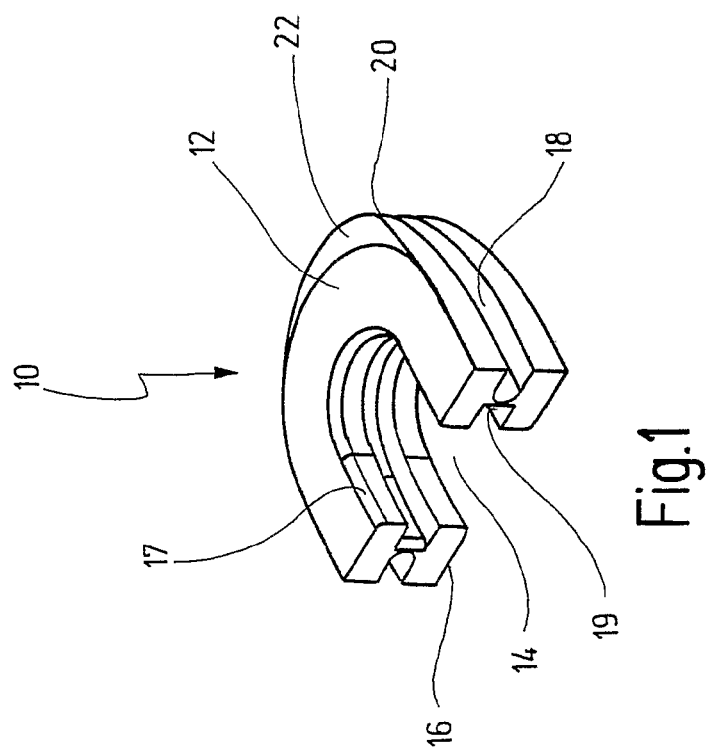
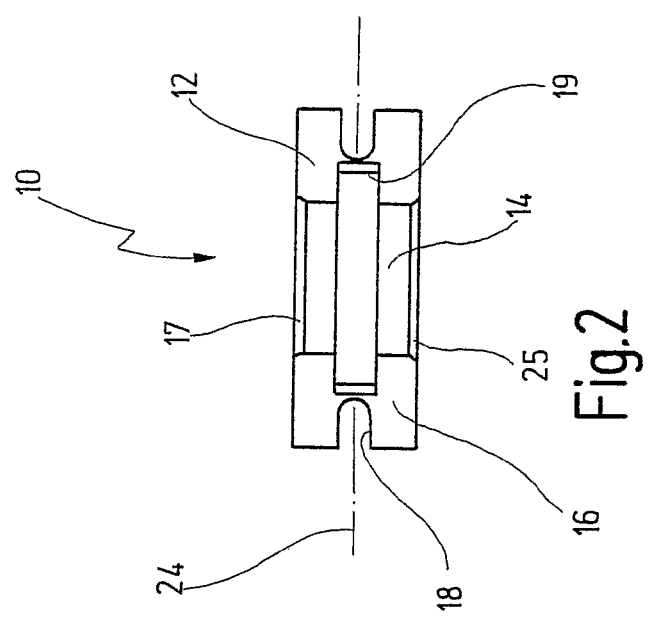

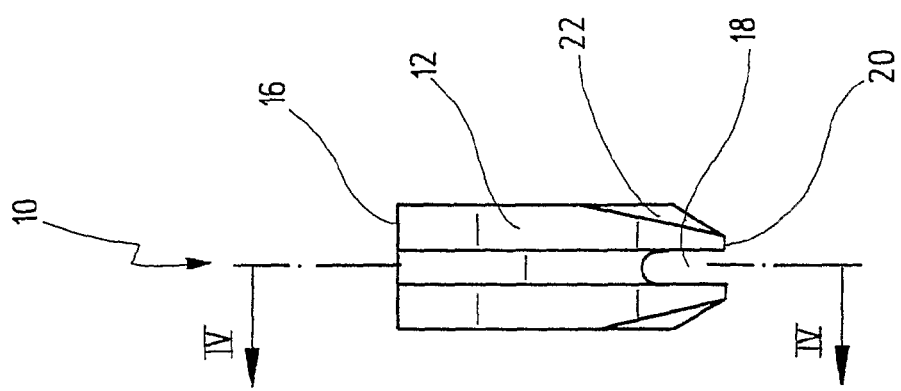
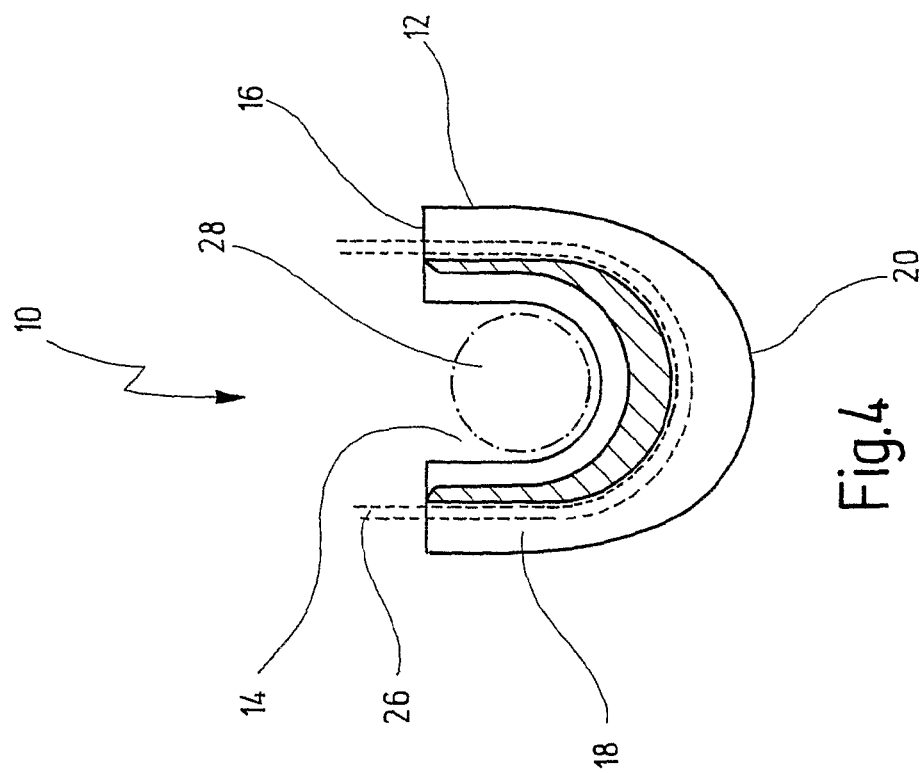

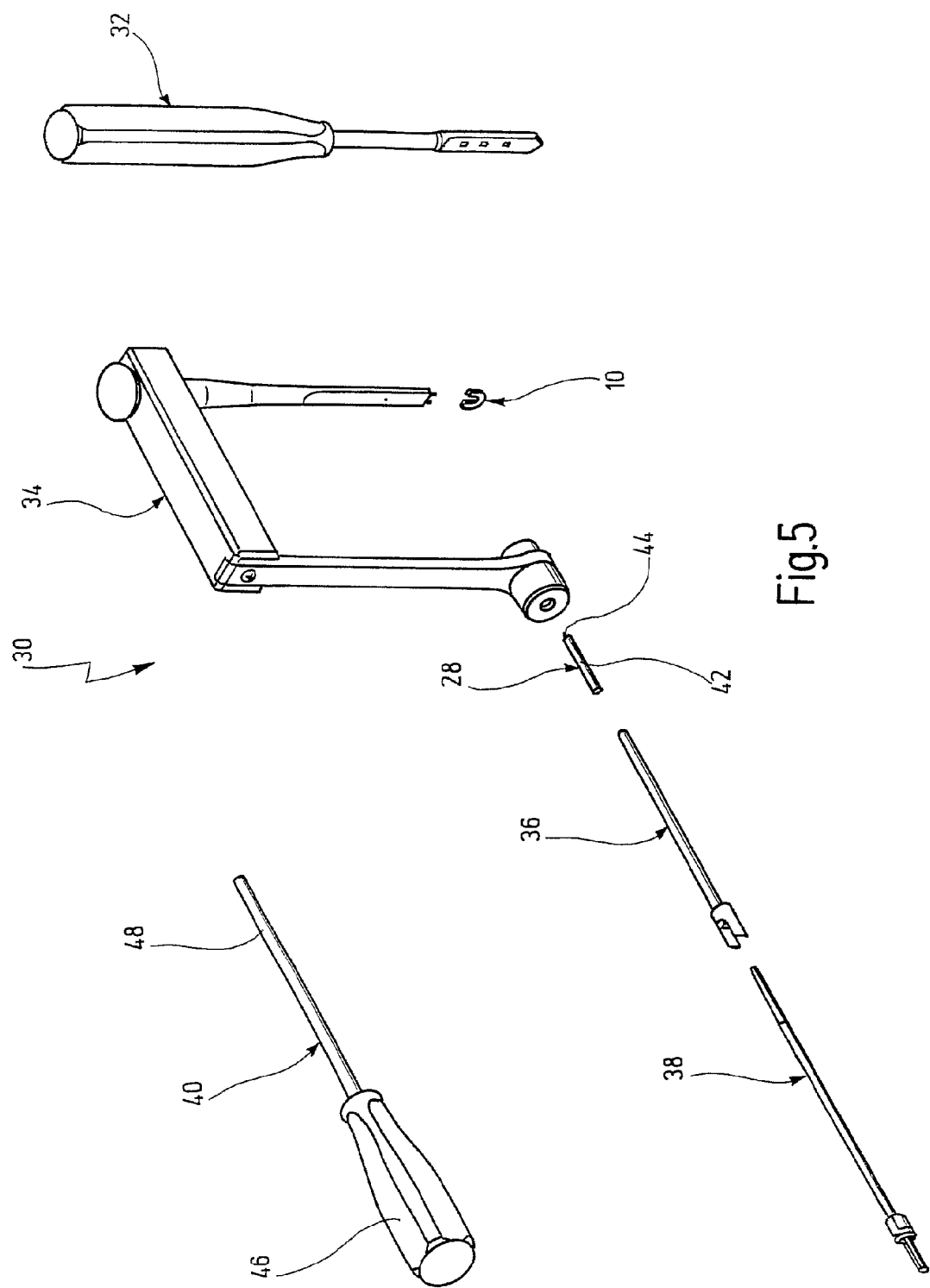

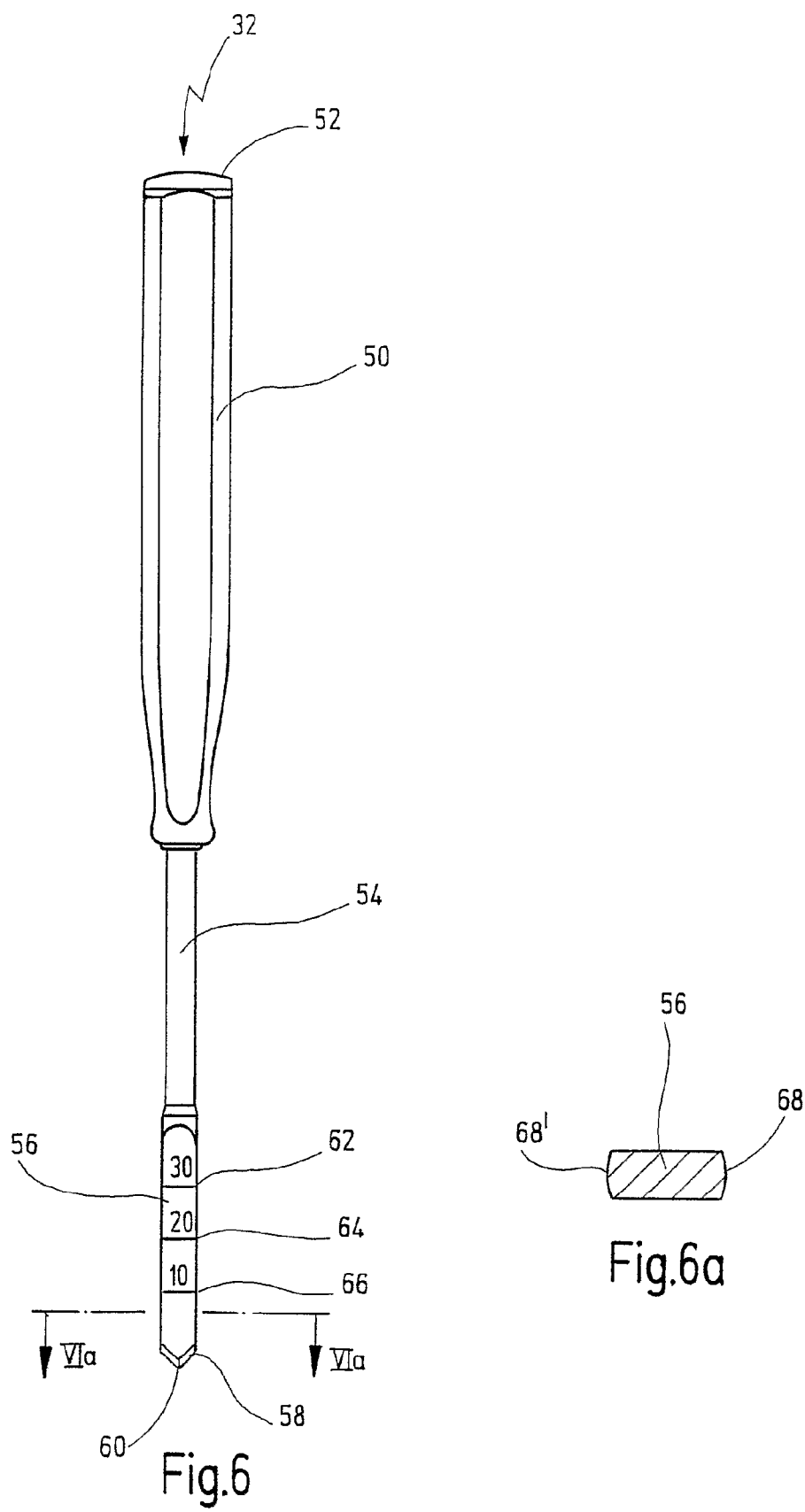

INSTRUMENT SET FOR FIXING AN IMPLANT IN A BONE

CROSS REFERENCE OF PENDING APPLICATION

This application is a continuation of pending international application PCT/EP2005/003431 filed on Apr. 1, 2005 which designates US and which claims priority of German patent application No. 10 2004 018 426.7 filed on Apr. 7, 2004.

BACKGROUND OF THE INVENTION

The present invention relates to an instrument set for fixing a cord-like implant in a bone, with a retaining element that can be inserted into the bone, which retaining element comprises a recess for receiving a transverse pin and is also used to fix the implant.

An instrument set of this kind is known from document US 2003/0065391 A1.

In modern surgery, cord-like implants frequently have to be fixed in a bone. In the reconstruction of the ligaments of the knee joint, for example, natural or artificial replacement ligaments are inserted into a channel in the femur and are fixed there by means of a transverse pin. Such a transverse pin is sometimes also referred to as a crosspin.

It is also known to anchor thread loops in a bone by means of a transverse pin and to use these thread loops, for example, to secure detached or torn segments of the rotator cuff to the head of the humerus. This securing can be done directly, that is to say by the thread loops themselves, or by means that are connected to the thread loops.

If cord-like implants of this kind are fixed in a channel in the bone only by means of the transverse pin, without a retaining element, the implant may move to and fro when subjected to loading. This to and fro movement compromises the implant's ability to take and can also lead to a rubbing of the implant on the transverse pin, which in extreme cases leads to a tearing of the implant.

It has therefore been attempted to reduce this to and fro movement by means of a retaining element.

A device and a method for reconstructing a knee ligament are known from document US 2003/0065391 A1 mentioned above. This device comprises a retaining element that has at least two through-openings. The first opening is used to receive the cord-like implant, while the second opening is used to receive the transverse pin.

For the reconstruction of a ligament in accordance with document US 2003/0065391 A1, the implant is guided through the proximal hole, and the retaining element is introduced by means of an applicator into a channel already formed in the femur. In a second step, the retaining element is then anchored in the femur by a transverse pin inserted into the distal hole of the retaining element.

Although the to and fro movement of a ligament in a bone channel can be considerably reduced by such a retaining element, this construction has the problem that the retaining element can be torn apart under high tensile loads, with the result that the ligament comes loose from the retaining element. The transverse pin and the remains of the retaining element then remain in the body.

In this case, these fragments have to be removed, and a new retaining element has to be fitted.

Therefore, an object of the invention is to develop an instrument set for fixing a cord-like implant in a bone it in such a way that a cord-like implant can be fixed in a bone with much greater safety and reliability.

SUMMARY OF THE INVENTION

According to an aspect of the invention, this object is achieved by the fact that the retaining element comprises a guide for receiving the implant, said guide being configured in such a way that the implant can be guided in a loop formation around the transverse pin distally from the retaining element.

If strong tensile forces cause the retaining element to break, this no longer leads to the cord-like implant being torn out, because the transverse pin then still secures it against being pulled out.

Since a failure of the retaining element caused by high loads also mostly takes place at the points of force introduction, which in case of a tensile load lie in the area of the apex of the loop, those parts of the guide that are located laterally of the implant are maintained, so that, even if the retaining element breaks, a to and fro movement of the implant is at least reduced, if in fact not completely avoided.

The looped guiding of the implant distally around the retaining element creates a relatively large contact surface between implant and retaining element. In this way, the danger of the implant rubbing on edge areas and tearing is considerably reduced.

An instrument set according to the invention, with such a retaining element, can therefore anchor an implant securely in a bone also over long periods of time. The retaining element remaining in the body is in this general sense the instrument set.

In another embodiment of the invention, the guide is configured as a guide that is open to the outside.

This can, for example, involve a groove into which the implant is placed.

This kind of guide has the advantage that the implant can simply be inserted from outside into the open guide, as a result of which the introduction of the implant into the guide is made very easy. This is particularly advantageous for stiff implants, for example wires, or also natural implants which are often slippy and difficult to handle.

This measure also has the advantage that the guide is easy to produce. A retaining element with an open guide can, for example, be produced by injection-molding directly in the desired form, or the guide can be milled, for example in the form of a groove, in a blank of the retaining element.

In another embodiment of the invention, the guide is configured as a closed guide.

A closed guide is to be understood as a guide whose circumference is completely closed at least along part of its length. The guide can be made tubular along its entire length, or it can be made up of individual tube sections. A slit can also be provided through which the implant can be clipped into the guide. It is also possible to produce a retaining element with an already-made implant in the form of a thread, said thread already being incorporated in the closed guide.

Since the guide is completely closed about the circumference at least along part of its length, it is no longer possible for the implant to fall or slide laterally out of the guide and thus come loose from the retaining element.

In another embodiment, a central axis of a transverse pin inserted into the recess is perpendicular to a loop plane defined by the guide.

This embodiment has the advantage that the retaining element can be made as small as possible, since the thread is wound in a loop formation around the transverse pin along the shortest possible extent.

In another embodiment, the retaining element has a U-shaped configuration.

A U-shaped configuration means that a distal portion of the retaining element is approximately semicircular, and a proximal portion of the retaining element is composed of two arms extending from distal to proximal.

The semicircular portion narrows in the distal direction, facilitating the insertion of the retaining element into a bone.

The arms of the proximal portion ensure that the retaining element does not twist about the transverse pin during or after implantation in the bone, which could lead to stress to the implant and to tissue connected to the implant.

Moreover, the arms of the proximal portion can advantageously be used for connecting the retaining element to an applicator.

In another embodiment, the guide extends round the recess by at least 180°.

The greater the angle at which the guide extends round the recess, the longer the distance on which the implant is guided. The longer the distance on which the implant is guided, the more reliably is the implant guided round the transverse pin.

Lengthening this distance also increases the contact surface of the implant on the retaining element. In this way, the load on the retaining element is distributed across a greater surface area, as a result of which the durability of the retaining element is enhanced.

In another embodiment, a proximal end of the retaining element has a quadrangular cross section.

This embodiment has the advantage that, if a retaining element configured in this way is inserted into a channel in a bone having the same cross section, this can only be done in certain positions. This means that the recess for receiving the transverse pin is located in exactly defined positions. This makes insertion of the transverse pin much easier and safer.

Twisting of the implant in the bone channel can also be avoided by means of this configuration.

In another embodiment, the retaining element narrows in the distal direction perpendicular to the loop plane.

Such narrowing gives the retaining element a wedge shape. Such a wedge shape simplifies the insertion of the retaining element into a bone channel, since the retaining element centers itself in the bone channel by way of its narrowing sides.

If a wedge-shaped retaining element is used, it is even possible to dispense with the formation of a bone channel and to drive the retaining element directly into the bone, in which case the distal end of the wedge acts as a blade for cutting the bone channel.

In another embodiment, the recess widens in a funnel shape in the direction of the transverse pin.

Such funnel-shaped widening of the recess at its edges facilitates the insertion of a transverse pin into this recess. The transverse pin no longer has to be inserted completely centered into the recess, and instead, when it meets the funnel-shaped edges, it is guided by these edges toward the center of the recess.

In another embodiment, the retaining element is made of biodegradable material.

Implants made of biodegradable material are slowly broken down after implantation in a bone and are replaced by regrowing endogenous tissue. This has the advantage that, after a certain period of time, the retaining element is completely replaced by endogenous tissue, which leads to a particularly reliable connection between the bone and the implant. However, if the retaining element degrades unevenly, or, because of the anatomical circumstances of the patient, too quickly, the transverse pin still secures the implant against becoming dislodged.

Moreover, retaining elements made of biodegradable material are generally better tolerated than retaining elements made of non-biodegradable material.

In another embodiment, the retaining element comprises elements for connecting it releasably to an applicator.

Using an applicator makes it easier to insert a small retaining element, often measuring only a few centimeters, into a long, narrow channel in the bone. By means of the abovementioned measure, the retaining element can be connected temporarily to an applicator. This assembly of retaining element and applicator can then be manipulated by an operating surgeon, without any danger of the retaining element coming loose from the applicator.

It is also possible for a retaining element which has been introduced into the bone, and which is still connected to the applicator, to be withdrawn from the bone if the operating surgeon is not happy with the position of the retaining element.

Once the retaining element has been inserted in the bone to the satisfaction of the operating surgeon and the transverse pin has been inserted into the recess, the applicator can be withdrawn from the bone channel, thereby releasing the connection, so that the retaining element remains in the bone.

In one configuration of this measure, the elements are configured as a locking mechanism.

A locking mechanism is here to be understood as any locking mechanism known to a person skilled in the art, for example a ball lock or spring-mounted locking fingers.

A locking mechanism has proven a particularly preferred configuration of the abovementioned measure since, on the one hand, the retaining element is fixedly connected to the applicator, while, on the other hand, after the retaining element has been secured with the transverse pin, no additional unlocking is necessary for separating the applicator from the retaining element.

In a particular embodiment of the aforementioned measure, the transverse pin is made of biodegradable material.

Implants made of biodegradable material are slowly broken down after implantation in a bone and are replaced by regrowing endogenous tissue. This has the advantage that, after a certain period of time, the transverse pin is completely replaced by endogenous tissue, which leads to a particularly reliable connection between the bone and the implant.

In another embodiment, the instrument set additionally comprises an applicator for inserting the retaining element into a bone.

Inserting a retaining element together with a cord-like implant into a bone is a difficult procedure in which the implant may come loose from the retaining element.

By means of such an applicator, a rigid assembly of retaining element and applicator can be created which can then be safely manipulated by an operating surgeon. The applicator thus makes it easier to insert the retaining element into the bone and permits a correction of the position of the retaining element. The applicator can be configured such that the retaining element is inserted, for example pushed, into an already prepared bone channel, or such that the applicator or the combination of applicator and retaining element create the bone channel.

In another embodiment of the abovementioned measure, the applicator comprises at least one first arm for inserting a retaining element into a bone, and at least one second arm for inserting a transverse pin into a bone.

This measure ensures that the transverse pin is always inserted in an exactly defined position relative to a retaining element secured on the applicator.

In another embodiment, the applicator comprises two first arms for inserting retaining elements. The two first arms are arranged such that recesses of retaining elements arranged on the first arms are in alignment.

By means of this measure, it is possible, in one operating step, to insert two retaining elements into a bone at a defined relative position to one another, and for these two retaining elements to be secured with a single transverse pin.

Arranging two retaining elements in a defined relative position has proven particularly advantageous in the repair of damage to the rotator cuff, since two implants, for example in the form of suture threads, can be inserted into the head of the humerus in one operating step, as a result of which large detached areas of a rotator cuff can be reconnected securely to the head of the humerus.

In another embodiment of the abovementioned measure, the two first arms are displaceable relative to one another along an alignment line of the recesses of the retaining elements arranged on the first arms.

By means of the abovementioned measure, it is possible to change the spacing of the first arms and, consequently, the relative position of the retaining elements to be inserted into the bone and, in this way, it is possible to adapt the applicator to different anatomical circumstances.

In another embodiment, the at least one second arm comprises a drill bushing.

Before the transverse pin is inserted in a defined relative position with respect to the recess of the one retaining element secured on the first arm, a bore can be formed in the bone by means of such a drill bushing, and this greatly facilitates the insertion of the transverse pin.

In another embodiment, the at least one first arm comprises elements for connecting it releasably to a retaining element.

By means of this measure, a retaining element can initially be fixedly connected to the applicator. This assembly of retaining element and applicator can then be manipulated by an operating surgeon, without any danger of the retaining element coming loose from the applicator.

It is also possible for a retaining element which has been introduced into the bone, and which is still connected to the applicator, to be withdrawn from the bone if the operating surgeon is not happy with the position of the retaining element.

Once the retaining element has been inserted in the bone to the satisfaction of the operating surgeon and the transverse pin has been inserted into the recess, the applicator can be withdrawn from the bone channel, with the retaining element remaining in the bone.

In one configuration of this measure, the elements are configured as a locking mechanism.

A locking mechanism is here to be understood as any locking mechanism known to a person skilled in the art, for example a ball lock or spring-mounted locking fingers.

A locking mechanism has proven a particularly preferred configuration of the abovementioned measure since, on the one hand, the retaining element is fixedly connected to the applicator, while, on the other hand, after the retaining element has been secured with the transverse pin, no additional unlocking is necessary for separating the applicator from the retaining element.

In another embodiment, the instrument set also comprises a drill for drilling a channel for a transverse pin, and in particular it also comprises a milling cutter for cutting a channel for a transverse pin.

Although a transverse pin can be driven into a bone simply by means of impaction, it is not always possible to cleanly position the transverse pin during this impaction. However, if a channel is created in the bone by means of a drill or a milling cutter or by a combination of the two, a path for insertion of the transverse pin is created, and a precise insertion of the transverse pin is ensured.

In another embodiment of the invention, the milling cutter is configured as a hollow milling cutter.

The configuration of the milling cutter as a hollow milling cutter has the advantage that, after a channel has been milled for the transverse pin, the latter can be guided through the lumen of the hollow milling cutter, said hollow milling cutter serving as an insertion aid for the transverse pin.

In another embodiment, the milling cutter can be coupled to the drill, said drill preferably protruding beyond the milling cutter in the coupled state.

By means of this measure, a channel having two different diameters can be created in a single drilling/milling operation. The first channel preferably has a diameter greater than that of the transverse pin, and the second channel has a diameter smaller than that of the transverse pin.

After the drilling/milling operation, the drill can then be removed from the lumen of the hollow milling cutter, and the transverse pin can be guided through the lumen of the hollow milling cutter. The transverse pin can thus be passed through the lumen of the hollow milling cutter, and through the channel of greater diameter, to the channel of smaller diameter and can then be inserted with a press fit into this second portion of the channel.

In another embodiment, the instrument set also comprises an impactor for creating a channel for a retaining element.

Using an impactor, it is possible to create channels that do not have a circular cross section. A channel with a noncircular cross section facilitates orientation of a retaining element in this channel and prevents twisting of the retaining element.

Moreover, an impactor has no movable parts, thus making it particularly easy to produce and to clean.

In another embodiment, the impactor has a cross section with a shape corresponding to a cross section of a retaining element, in particular a cross section that is smaller than the cross section of the retaining element.

Using an impactor having a cross section corresponding to that of the retaining element, it is possible to create a channel corresponding to that of the retaining element. Thus, a bone channel can be created in which the retaining element can be inserted in a defined position, This facilitates the insertion of the transverse pin, since the retaining element, and consequently the recess of the retaining element, are always located in the same defined position.

If the cross section of the impactor is smaller than that of the retaining element, it is possible to provide the bone with a channel in which a retaining element is inserted with a press fit. In this way the retaining element is introduced fixedly into the channel. This prevents movements of the retaining element that could damage the retaining element or could loosen the transverse pin from its anchored position.

In another embodiment, the impactor has a quadrangular cross section.

Using an impactor with a quadrangular cross section, it is possible to create a channel having a quadrangular cross section. Such a channel has the advantage that, if a square retaining element is inserted, the latter can be inserted into the channel in a defined position and secure against twisting.

In another embodiment, the impactor comprises at least one graduation at a distal portion.

By means of such a graduation, the depth of insertion of the impactor, and thus the depth of the channel, is made visible to an operating surgeon quickly and in a simple manner.

In another embodiment, the impactor has a fork-shaped configuration.

By means of this measure it is possible, using one impactor, to create two or more channels in a bone in one operating step. The channels in this case are formed in the bone in exactly defined positions relative to one another.

This measure proves particularly expedient in combination with an applicator having two or more arms for inserting a retaining element, since in this way two or more channels can be created into which, in one operating step, two or more retaining elements can then be inserted and secured with a single transverse pin.

In another embodiment, the instrument set also comprises a ram for positioning a transverse pin in a bone.

Such a ram has a shaft whose cross section corresponds to the cross section of a transverse pin, and it is used to position a transverse pin with precision in a bone. Particularly if the transverse pin is inserted into a channel of smaller diameter, the ram can be used to press or drive the transverse pin into this channel.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

Illustrative embodiments of the invention are explained in more detail in the following description and are depicted in the drawing, in which:

FIG. 1 shows a perspective view of a retaining element;

FIG. 2 shows a plan view of the proximal end of the retaining element from FIG. 1;

FIG. 3 shows a side view of the retaining element from FIG. 2;

FIG. 4 shows a section through the retaining element from FIG. 3, along the line IV-IV;

FIG. 5 shows an exploded view of an instrument set for fixing a cord-like implant in a bone;

FIG. 6 shows the impactor of the instrument set from FIG. 5;

FIG. 6a shows a section through the impactor from FIG. 6, along the line VIa-VIa;

DETAILED DESCRIPTION OP PREFERRED EMBODIMENTS

Figure 7:
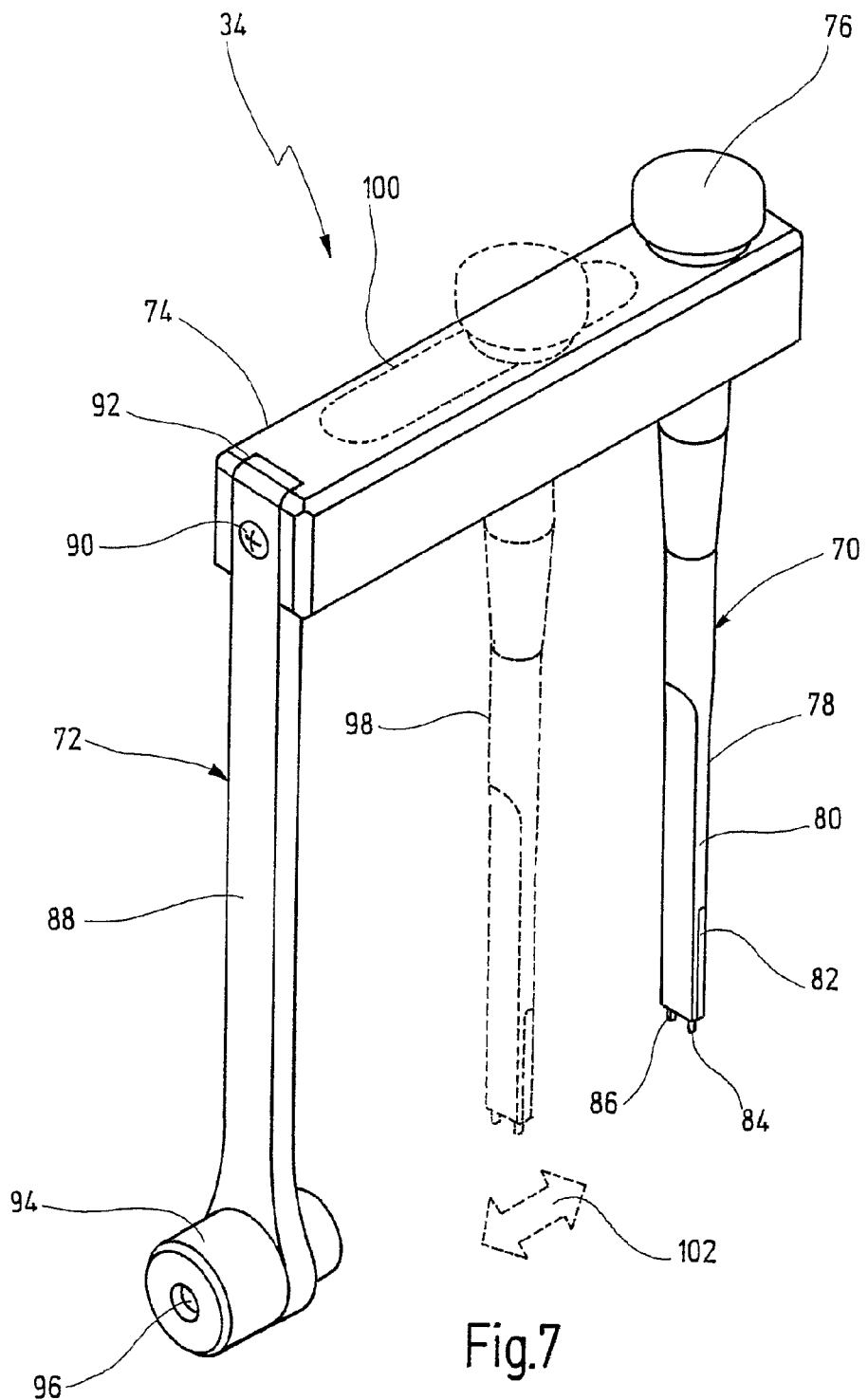
FIG. 7 shows the applicator of the instrument set from FIG. 5.

In FIG. 1, a retaining element is designated in its entirety by reference number 10.

The retaining element 10 has a U-shaped body 12 in whose center a recess 14 is arranged. The retaining element 10 is made from a biodegradable material, in this case a polylactic acid polymer.

The recess 14 opens in the direction of a proximal end 16 of the body 12. An edge 17 of the recess 14 is beveled, as a result of which the edge of the recess 14 has a profile that widens in the shape of a funnel.

A groove 18 is formed in the circumference of the outer contour surface of the U-shaped body 12. The groove 18 has a likewise U-shaped profile. This groove 18 forms a guide for a cord-like implant. It is clear to a man of the art that this groove 18 can be also partially or completely covered i.e. forming a channel to form a closed guide.

A groove 19 is formed in the inner contour of the body 12. This groove 19 has a square profile. This groove 19 is used for connecting the retaining element 10 to an applicator.

A crescent-shaped portion 22 is situated at a distal end 20 of the body 12. This crescent-shaped portion 22 is beveled, as a result of which the thickness of the body 12 decreases in the distal direction in the area of the crescent-shaped portion 2Z.

FIG. 2 shows a plan view of the proximal end 16 of the body 12 of the retaining element 10.

The dot-and-dash line indicates a loop plane 24, which is defined by the groove 18.

It can be seen from this view that, on the side opposite the edge 17, the recess 14 has another beveled edge 25. Thus, the recess 14 has a funnel-shaped profile on both sides.

This view once again shows the U-shaped profile of the outer groove 18 and the square profile of the inner groove 19.

FIG. 3 shows a side view of the retaining element 10. It can be seen here that the body 12 of the retaining element 10 narrows toward the distal end 20 in the crescent-shaped area 22, as a result of which the distal end 20 has a wedge-shaped profile.

This figure also shows that the groove 18 is particularly deep in the area of the distal end 20 of the body 12, thereby guaranteeing particularly secure guiding of an implant.

FIG. 4 shows a section through a retaining element 10 along the line IV-IV from FIG. 3. Moreover, a cord-like implant 26 is indicated by the broken line, and a transverse pin 28 is indicated by the dot-and-dash line.

The implant 26 is guided distally around the transverse pin 28 by the groove 18. It can be seen here that the groove 18 is much deeper in the area of the distal end 20 of the retaining element than in the area of the proximal end 16.

The transverse pin 28 is received in the recess 14 of the retaining element 10.

If the body 12 of the retaining element 10 was to fail under a tensile load of the implant 26 in the direction of the distal end 16 of the retaining element 10, the implant 26 is clearly still secured by the transverse pin 28.

In FIG. 5, an instrument set for fixing a cord-like implant in a bone is designated in its entirety by reference number 30.

The instrument set 30 comprises a retaining element 10, as has already been shown in FIGS. 1 to 4.

The instrument set 30 also comprises a transverse pin 28, as has already been shown in FIG. 4.

Moreover, the instrument set 30 comprises an impactor 32, an applicator 34, a hollow milling cutter 36, a drill 38 and a ram 40.

The transverse pin 28 has a cylindrical body 42 that narrows in the distal direction towards a tip 44.

The ram 40 has a grip 46 and a shaft 48. The shaft 48 thereby has the same cross section as the body 42 of the transverse pin 28. The grip 46 of the ram 40 is configured in such a way that the ram 40 can be used to position a transverse pin 28 in a bone by means of a hammer.

FIG. 6 shows the impactor 32 of the instrument set 30 from FIG. 5 in greater detail.

The impactor 32 has a grip 50. The grip 50 has a proximal end 52, which is configured in such a way that the impactor 32 can be driven into a bone by means of a hammer.

In the distal direction, the grip 50 is adjoined by a shaft 54, which merges distally into a chisel portion 56. At its distal end, the chisel portion 56 has blades 58 that run together to a tip 60. The blades 58, in combination with the tip 60, cut a bone channel in a bone while the impactor 32 is being driven in.

The chisel portion 56 also has graduations 62, 64 and 66. These graduations 62, 64 and 66 permit simple monitoring of the depth of insertion of the impactor 32 into a bone.

FIG. 6a shows a section through the impactor 32 along the line VIa-VIa from FIG. 6.

It is clear from this view that the chisel portion 56 of the impactor 32 has a substantially rectangular cross section. The impactor 32 can therefore be used to cut into the bone a channel that has a substantially rectangular cross section. This rectangular cross section of the bone channel, in combination with the rectangular area of the proximal end 16 of the retaining element 10, makes it possible to insert the retaining element into the bone in an exactly defined position.

The cross section of the chisel portion 56 is slightly smaller than that of the proximal end 16 of the retaining element 10, such that the impactor 32 can be used to create a channel in which the retaining element 10 is inserted with a press fit.

The narrow sides 68, 68' of the chisel portion 56 have a convex configuration. This makes it possible to insert a retaining element 10 with an implant 26 which to a certain extent protrudes beyond the groove 18 of the retaining element 10.

FIG. 7 shows the applicator 34 of the instrument set 30 from FIG. 5.

The applicator 34 has a first arm 70 for introducing a retaining element 10 into a bone, and a second arm 72 for introducing a transverse pin 28 into a bone. The first arm 70 and the second arm 72 are connected to one another by a connecting element 74.

At its proximal end, the arm 70 has a knob 76, which is configured in such a way that the arm 70 can be driven into a bone channel by means of a hammer.

The distal portion 78 of the arm 70 has an approximately rectangular cross section. The cross section of the distal portion 78 corresponds to the cross section of the chisel portion 56 of the impactor 32.

A recess 82 is formed in a narrow side 80 of the distal portion 78 of the arm 70. This recess 82 is used to guide an implant 26 along the distal portion 78 without it protruding beyond the side 80.

Two spring-mounted locking fingers 84 and 86 are arranged at the end of the distal portion 78 of the arm 70 and are provided for connecting a retaining element 10 to the arm 70.

The second arm 72 has a substantially rectangular body 88 which, at its proximal end, is connected to the connecting element 74 by means of a screw 90. The body 88 of the arm 72 comes to lie in a recess 92 of the connecting element 74, as a result of which the arm 72 is connected to the connecting element 74 in a manner secure against twisting.

The arm 72 has a drill bushing 94 at its distal end. This drill bushing has a lumen 96 which is perpendicular to the body 88 of the arm 72. The lumen 96 of the drill bushing 94 is arranged such that it is in alignment with a recess 14 of a retaining element 10 arranged on the arm 70.

A second embodiment of the applicator 34 is indicated by the broken lines. This second embodiment comprises a further arm 98 that corresponds to the first arm 70.

This arm 98 is displaceable along an oblong hole 100 in the connecting element 74 in the direction of the double arrow 102. The arm 98 is arranged such that a recess 14 of a retaining element 10 arranged on the arm 98 is in alignment with a recess 14 of a retaining element 10 arranged on the arm 70. The recesses of the two retaining elements are in turn in alignment with the lumen 96 of the drill bushing 94.

By means of an applicator configured in this way, two retaining elements 10 can be introduced into a bone in a defined relative position to one another and can be secured there with a single transverse pin 28.

Figure 8:
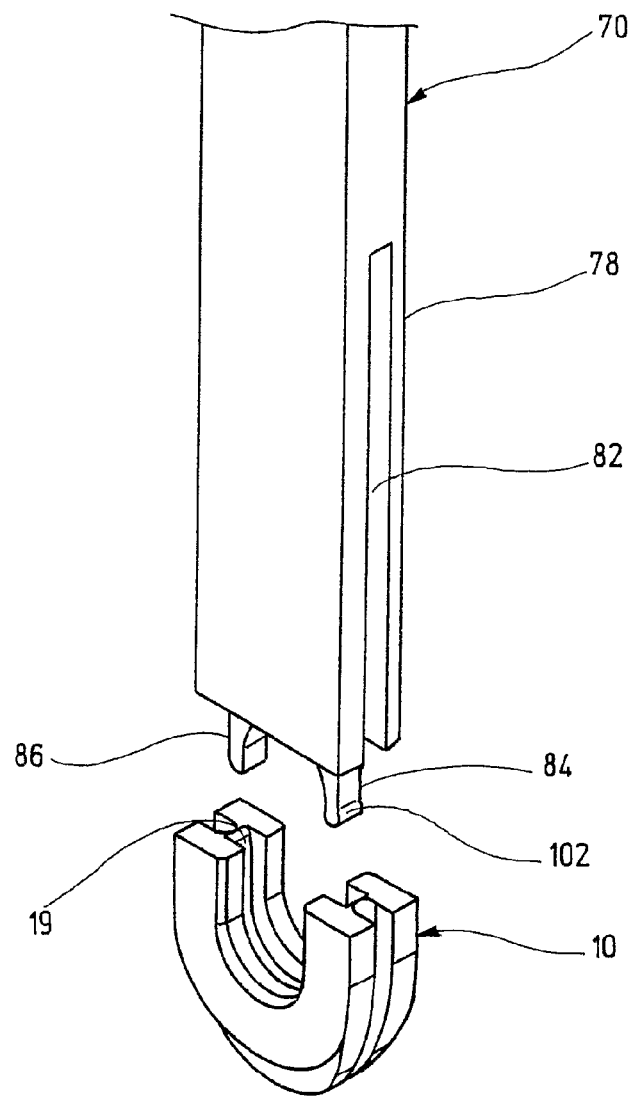
FIG. 8 shows an enlarged view of a portion of the applicator from FIG. 7 together with the retaining element from FIG. 1.

FIG. 8 shows an enlarged view of the distal portion 78 of the first arm 70 of the applicator 34. The retaining element 10 is also shown.

It is clear from this view that the locking fingers 84 and 86 are arranged in such a way that they can engage in the groove 19 in the inner contour of the retaining element 10.

The retaining finger 84 has a bead 102 which ensures the secure connection between the locking finger 84 and the groove 19. The retaining finger 86 has a similar bead which, however, cannot be seen in this view.

Figure 9:
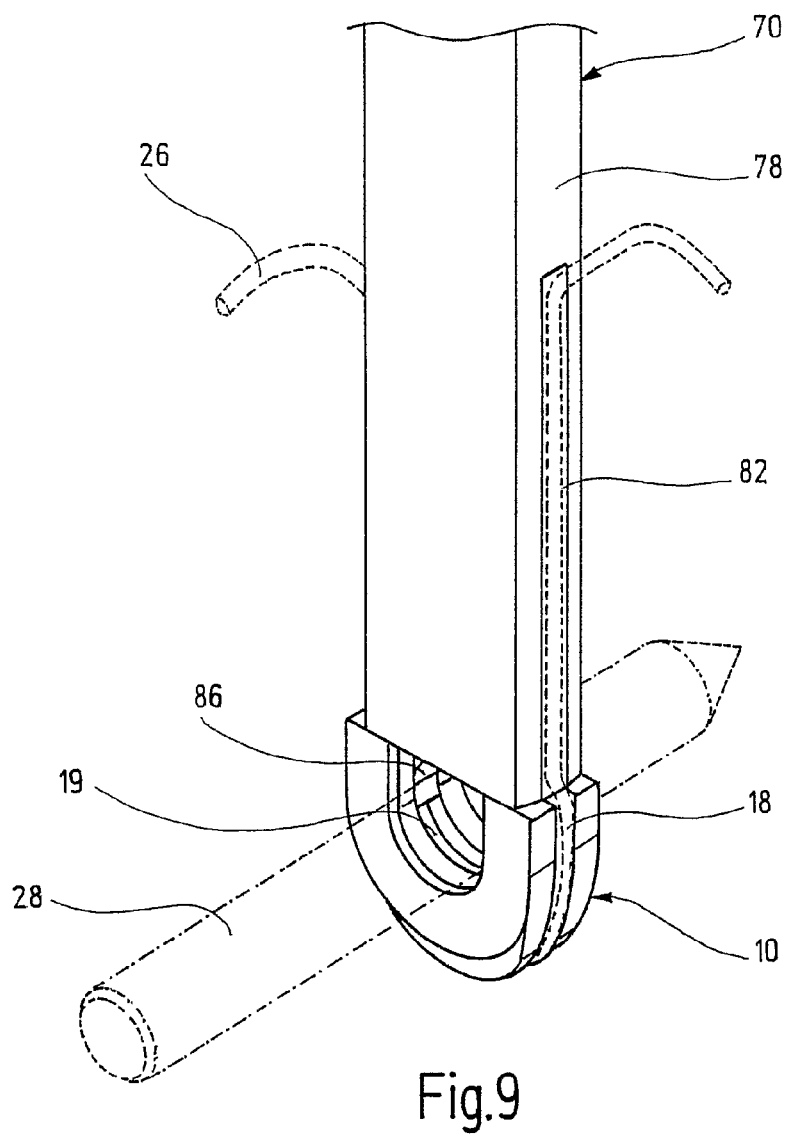
FIG. 9 shows the portion from FIG. 8, the retaining element being arranged on said portion.

FIG. 9 shows a proximal portion 78 of the arm 70 of the applicator 34, a retaining element 10 being arranged at the distal end of the arm 70. The locking finger 86 engages here in the groove 19 of the retaining element 10, thereby guaranteeing a secure connection between the retaining element 10 and the arm 70.

The broken lines indicate a cord-like implant 26 which runs round the distal portion 78 of the arm 70 and the retaining element 10 and comes to lie in the groove 18 and in the recess 82.

The dot-and-dash lines indicate a transverse pin 28 which is guided through the recess 14 of the retaining element 10, the proximal end of the recess 14 being limited by the distal end of the arm 70.

In the state indicated by the broken lines and dot-and-dash lines, the retaining element 10 and the implant 26 are secured by the transverse pin 28, and the arm 70 can be withdrawn from the retaining element 10.

Figure 10:
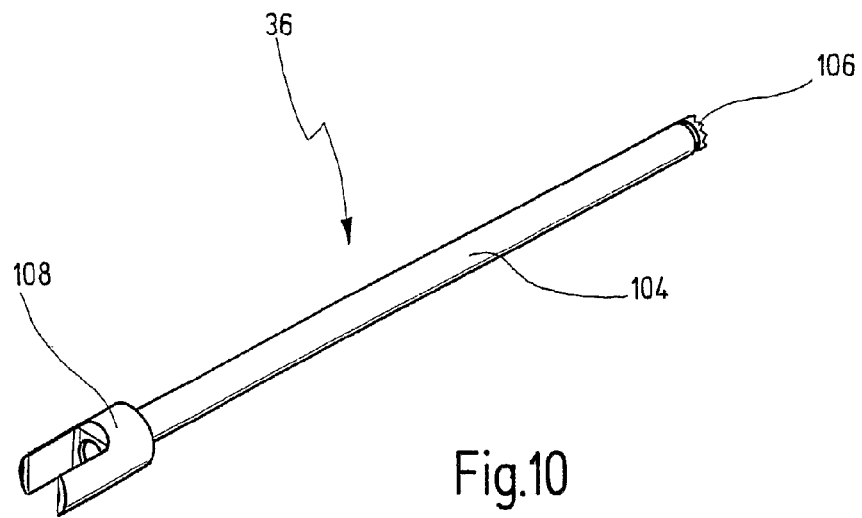
FIG. 10 shows the hollow milling cutter of the instrument set from FIG. 5.

FIG. 10 shows the hollow milling cutter 36 of the instrument set 30 from FIG. 5.

The hollow milling cutter 36 has a hollow shaft 104, the clear internal diameter of the hollow shaft 104 corresponding approximately to the diameter of the body 12 of the transverse pin 28. At a distal end, the hollow shaft 104 comprises an annular cutter head 106. At a proximal end, the hollow shaft 104 comprises a coupling element 108 which is provided for coupling the milling cutter 36 to the drill 38.

Figure 11:
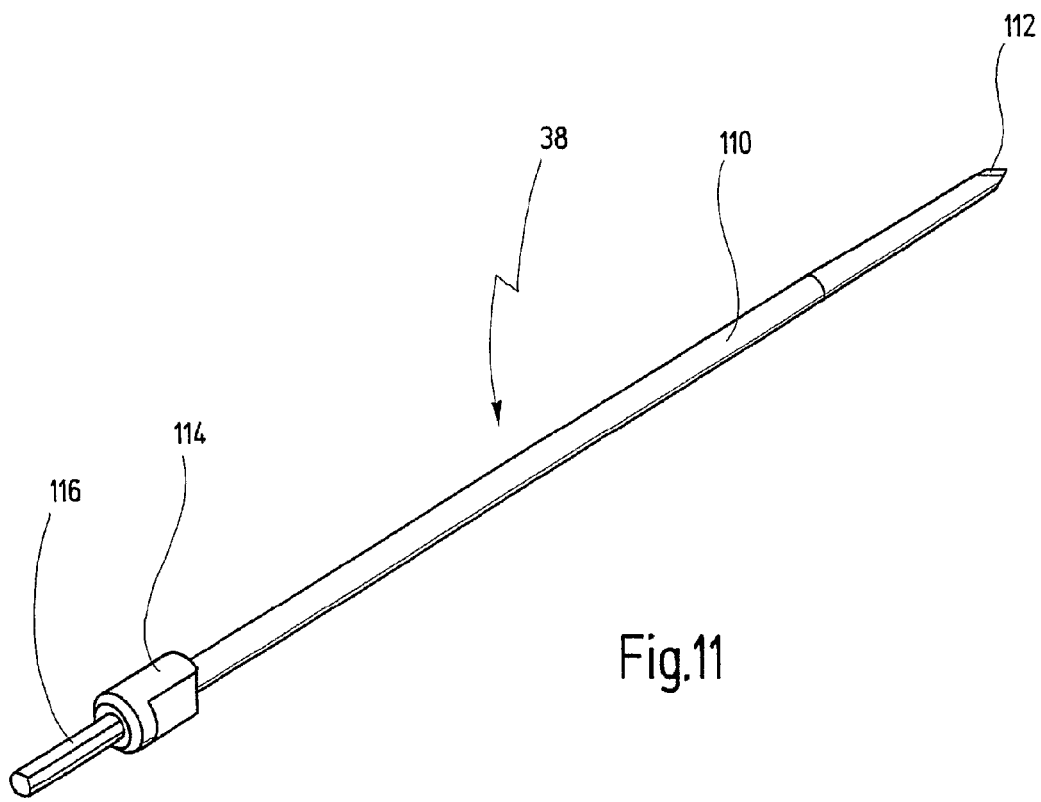
FIG. 11 shows the drill of the instrument set from FIG. 5.

FIG. 11 shows the drill 38 of the instrument set 30 from FIG. 5.

The drill 38 has a shaft 110 whose diameter corresponds approximately to the clear internal diameter of the hollow shaft 104 of the milling cutter 36. A blade 112 for drilling a bone channel is provided at a distal end of the shaft 110. At a proximal end of the shaft there is a coupling element 114 which is provided for bringing the drill 38 into operative connection with the milling cutter 36.

Adjoining the coupling element 114 in the proximal direction, there is a section 116 which has a hexagonal cross section and which is used for connecting the drill 38 to a drilling machine.

The drill 38 can be coupled to the milling cutter 36 by introducing the shaft 110 of the drill 38 into the hollow shaft 104 of the milling cutter 36. The coupling element 114 of the drill 38 then comes to lie in the coupling element 108 of the milling cutter 36, thereby creating an operative connection between the drill 38 and the milling cutter 36.

In the assembled state, part of the shaft 110 of the drill 38 protrudes beyond the distal end of the shaft 104 of the milling cutter 36. This assembly can be used to drill a channel having two portions with different diameter.

After the drilling/milling operation is completed, the drill 38 can be removed from the tubular shaft 104 of the milling cutter 36, said milling cutter 36 remaining in the bone. In a second operating step, a transverse pin 28 can then be inserted through the hollow shaft 104 of the milling cutter 36 and into the bone.

Figure 12:
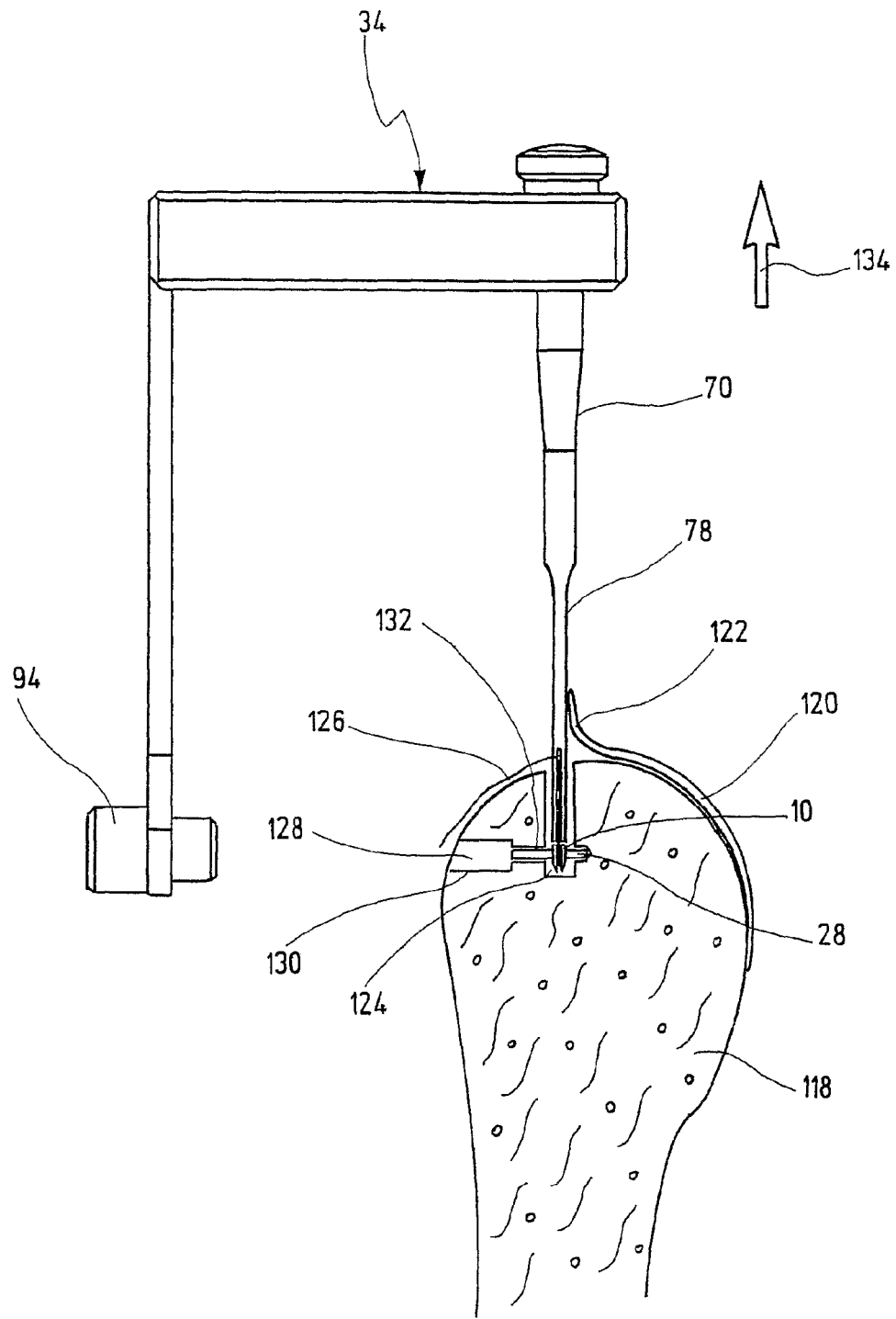
FIG. 12 shows a schematic view of a section through a head of a humerus, with a retaining element having been inserted.

FIG. 12 is a schematic cross section through a head 118 of a humerus.

On the outside face of the head 118 of the humerus, there is a rotator cuff 120, the latter having a portion 122 that has become detached from the head 118 of the humerus and is to be reconnected to it. To do this, a first channel 124 was driven into the head 118 of the humerus by means of the impactor 32 and a hammer. The arm 70 of the applicator 34, at whose distal end the retaining element 10 is arranged, was inserted into this channel 124. An implant in the form of a thread 126 runs round the retaining element 10 and part of the distal portion 78 of the arm 70.

By means of the drill 38 and the milling cutter 36, a second channel 128 was then drilled/milled into the head 118 of the humerus. The drill bushing 94 of the applicator 34 ensured the alignment of the channel 128 with the recess 14 of the implant 10. The second channel 128 has a first portion 130 with a greater diameter, and a second portion 132 with a smaller diameter. After the drilling/milling operation, the drill 38 was removed from the shaft of the milling cutter 36.

The transverse pin 28 was introduced through the shaft 104 of the milling cutter 36 and into the channel 128 and then positioned, by means of the ram 40, in the second portion 132 of the second channel 128. The transverse pin 28 thus secures the implant 10 and the thread 126 in the head 118 of the humerus.

The applicator 34 can now be removed from the head 118 of the humerus in the direction of the arrow 134, and the portion 122 of the rotator cuff 120 can be reconnected to the head 118 of the humerus by means of the thread 126.

Figure 13:
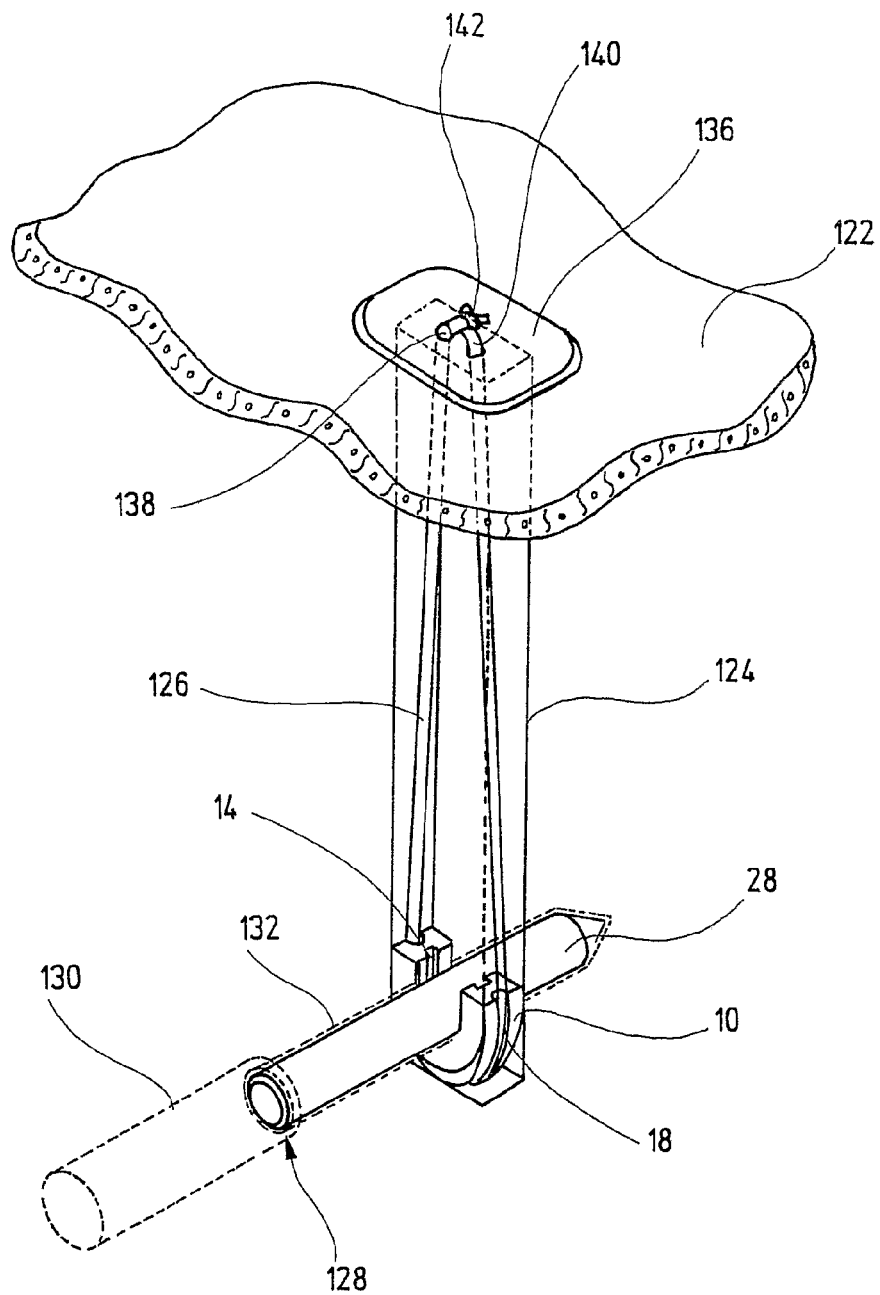
FIG. 13 shows a schematic view of a portion of a rotator cuff secured by a retaining element.

FIG. 13 shows a schematic representation of the portion 122 of the rotator cuff that has been reconnected to the head 118 of the humerus by means of the retaining element 10, the transverse pin 28 and the thread 126.

The retaining element 10 sits with a press fit in the channel 124, said channel 124 having substantially the same cross section as the retaining element 110, but with the cross section of the channel 124 being slightly smaller.

The retaining element 10 is secured by the transverse pin 28 which is inserted into the second channel 128 indicated by the broken lines, the transverse pin 28 having been transferred completely from the portion 130 of large diameter of the second channel 128 into the channel 132 of small diameter of the second channel 128 and being held in a press fit in this portion 132. The transverse pin 28 comes to lie in the recess 14 of the retaining element 10.

The thread 126 runs round the transverse pin 28 and the retaining element 10, said thread 126 coming to lie in the groove 18 of the retaining element 10. The thread 126 is thus arranged in the channel 124 such that it is secured against displacement along the center axis of the pin 28.

If the retaining element 10 were now to fail, the thread 126 would still be secured by the transverse pin 28.

The two ends of the thread 126 were guided through that portion 122 of the rotator cuff to be fastened in place and were secured against tearing out by means of a plate 136. The two ends of the thread 126 were for this purpose guided through the holes 138 and 140 of the plate 136 and connected to one another by means of a knot 142.

The plate 136 is used to avoid a cutting of the rotator cuff 122 by the thread 126. The portion 122 of the rotator cuff is in this way once again connected securely to the head 118 of the humerus.

It is also possible to insert a thread that has already been prepared as a closed annular thread. The annular thread is wound as a double strand round the detached portion of the rotator cuff and pulled once through itself. In this way, the thread is already connected to the portion that is to be fixed.

The retaining element is threaded into the remaining loop and driven into the bone, the size of this loop determining the depth of insertion.

What is claimed is:

1. An instrument set for fixing cord-like implants in a bone, comprising
   two retaining elements that can be inserted into said bone, each having
      a distal end,
      a proximal end, and
      a recess for receiving a transverse pin having a central axis;
   each of said retaining elements being used to fix each of said implants,
   each of said retaining elements being made of biodegradable material,
   each of said retaining elements further comprising
      a guide defining a loop plane, for receiving said implant, said guide being configured in such a way that said implant can be guided in a loop formation around said transverse pin distally from each of said retaining elements,
   said instrument set further comprising an applicator for inserting each of said retaining elements into said bone, wherein said applicator comprises two first arms for inserting each of said retaining elements into said bone, and a second arm for inserting said transverse pin into said bone.

2. The instrument set of claim 1, wherein said guide is configured as an open guide.

3. The instrument set of claim 1, wherein said guide is configured as a closed guide.

4. The instrument set of claim 1, wherein said central axis of said transverse pin inserted into said recess is perpendicular to said loop plane defined by said guide.

5. The instrument set of claim 1, wherein each of said retaining elements has a U-shaped configuration.

6. The instrument set of claim 1, wherein said guide extends around said recess by at least 180 degrees.

7. The instrument set of claim 1, wherein said proximal end of each of said retaining elements has a quadrangular cross section.

8. The instrument set of claim 1, wherein each of said retaining elements narrows perpendicular to said loop plane in a distal direction.

9. The instrument set of claim 1, wherein said recess widens in a funnel shape in a direction of said transverse pin.

10. The instrument set of claim 1, wherein each of said retaining elements comprises elements for connecting it releasably to said applicator.

11. The instrument set of claim 10, wherein said elements are configured as a locking mechanism.

12. The instrument set of claim 1, wherein said two first arms are arranged such that said recesses of said retaining elements arranged on said first arms are in alignment forming an alignment line.

13. The instrument set of claim 12, wherein said two first arms are displaceable relative to one another along said alignment line of said recesses of said retaining elements arranged on said first arms.

14. The instrument set of claim 1, wherein said second arm comprises a drill bushing.

15. The instrument set of claim 1, wherein each of said two first arms comprises elements for connecting them releasably to one of said retaining elements.

16. The instrument set of claim 15, wherein said elements are configured as a locking mechanism.

17. The instrument set of claim 1, further comprising a drill for drilling a channel for said transverse pin.

18. The instrument set of claim 17, further comprising a milling cutter for cutting a channel for said transverse pin.

19. The instrument set of claim 18, wherein said milling cutter is configured as a hollow milling cutter.

20. The instrument set of claim 19, wherein said milling cutter can be coupled to said drill.

21. The instrument set of claim 20, wherein said drill protrudes beyond said milling cutter in a coupled state.

22. The instrument set of claim 1, further comprising an impactor for creating a channel for each of said retaining elements.

23. The instrument set of claim 22, wherein said impactor has a cross section with a shape corresponding to a cross section of each of said retaining elements.

24. The instrument set of claim 23, wherein said cross section of said impactor is smaller than said cross section of each of said retaining element.

25. The instrument set of claim 22, wherein said impactor has a quadrangular cross section.

26. The instrument set of claim 22, wherein said impactor comprises a distal portion comprising at least one graduation.

27. The instrument set of claim 22, wherein said impactor has a fork-shaped configuration.

28. The instrument set of claim 1, further comprising a ram for positioning said transverse pin in said bone.

* * * * *